United States Patent [19]

Coviello et al.

[11] 4,179,616

[45] Dec. 18, 1979

[54] APPARATUS FOR SANITIZING LIQUIDS WITH ULTRA-VIOLET RADIATION AND OZONE

[75] Inventors: Allan J. Coviello; Frederick E. Bernardin, Jr., both of Ann Arbor; Robert R. Rohrkemper, Chelsea, all of Mich.

[73] Assignee: Thetford Corporation, Ann Arbor, Mich.

[21] Appl. No.: 947,505

[22] Filed: Oct. 2, 1978

Related U.S. Application Data

[63] Continuation of Ser. No. 879,204, Feb. 21, 1978, abandoned.

[51] Int. Cl.² .......................... C02B 1/00; C02B 1/38; C02B 3/08; H01J 61/52
[52] U.S. Cl. ................................ 250/527; 210/63 Z; 210/177; 210/259; 250/541; 250/538; 250/504; 250/436; 250/429; 313/24; 313/36; 313/44; 422/186; 422/198; 422/305
[58] Field of Search ............... 250/538, 541, 436, 429, 250/438, 504, 527; 210/63 Z, 177, 253, 256, 258, 259; 313/24, 36, 44; 62/264; 422/24, 121, 129, 186, 198, 305

[56] References Cited

U.S. PATENT DOCUMENTS

| | | | |
|---|---|---|---|
| 1,435,192 | 11/1922 | Anderson | 313/24 |
| 2,295,046 | 9/1942 | Noel | 313/24 |
| 3,336,099 | 8/1967 | Czulak et al. | 210/169 |
| 3,603,827 | 9/1971 | Degawa | 313/36 |
| 3,659,096 | 4/1972 | Kompanek | 73/141 A |
| 3,665,235 | 5/1972 | Hugot | 313/24 |
| 4,033,719 | 7/1977 | Conn et al. | 210/169 |
| 4,090,960 | 5/1978 | Cooper | 210/63 Z |
| 4,101,424 | 7/1978 | Schooley et al. | 250/504 |
| 4,141,830 | 2/1979 | Last | 210/63 Z |

FOREIGN PATENT DOCUMENTS

| | | |
|---|---|---|
| 2225984 | 12/1973 | Fed. Rep. of Germany |
| 2307877 | 9/1974 | Fed. Rep. of Germany |
| 2551622 | 6/1977 | Fed. Rep. of Germany |

*Primary Examiner*—Joseph Scovronek
*Assistant Examiner*—Bradley R. Garris
*Attorney, Agent, or Firm*—Olsen and Stephenson

[57] ABSTRACT

Apparatus for contacting contaminated water with ultra-violet light to eliminate potentially harmful organisms as well as to provide air cooling necessary for efficient operation of the UV lamp and simultaneous production of ozone in the apparatus for secondary disinfection of the water, the water after treatment by the ultraviolet light being discharged into a water storage tank, and the irradiated air that contains the ozone being discharged into the tank into contact with the water for carrying out the secondary disinfection.

16 Claims, 7 Drawing Figures

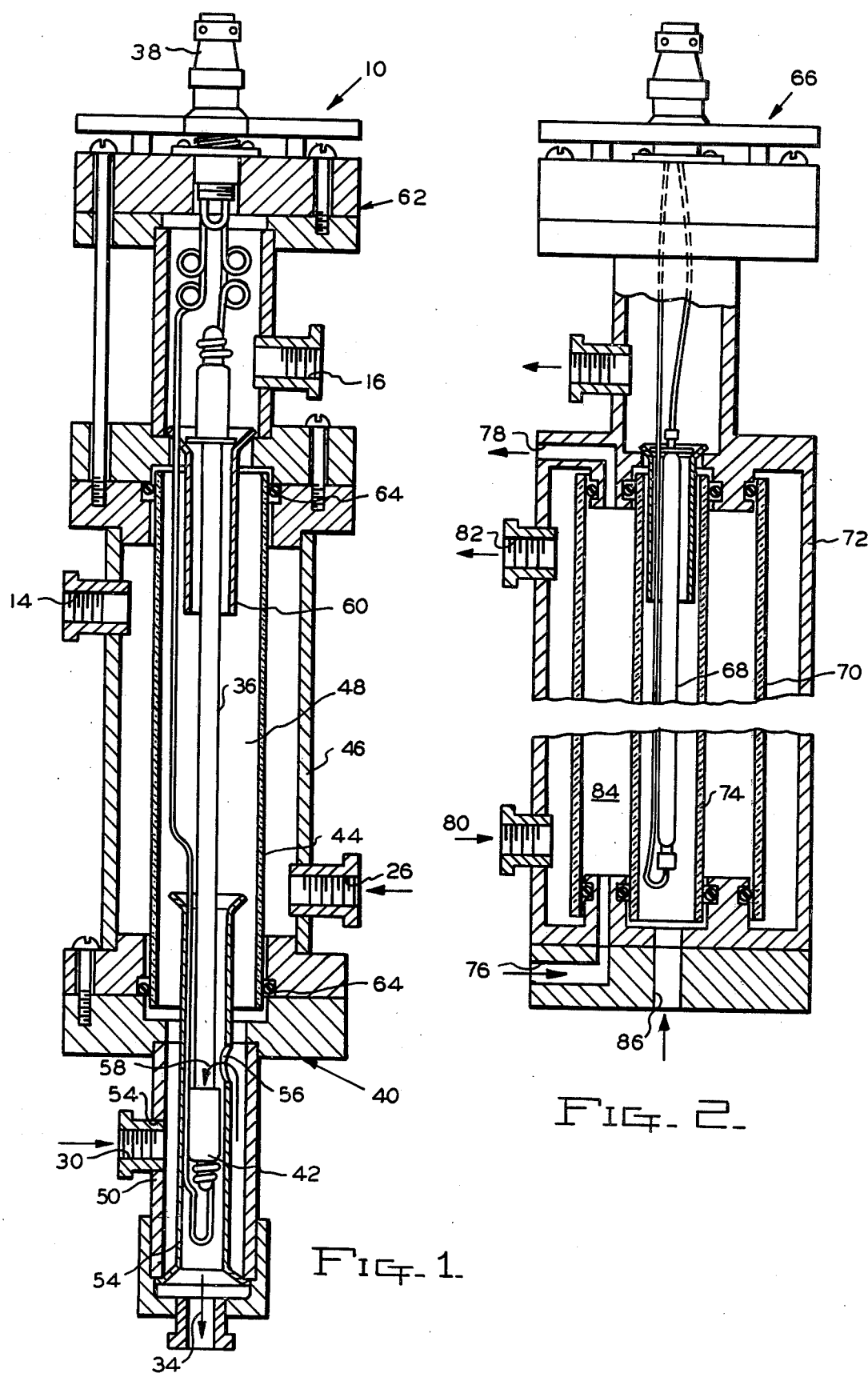

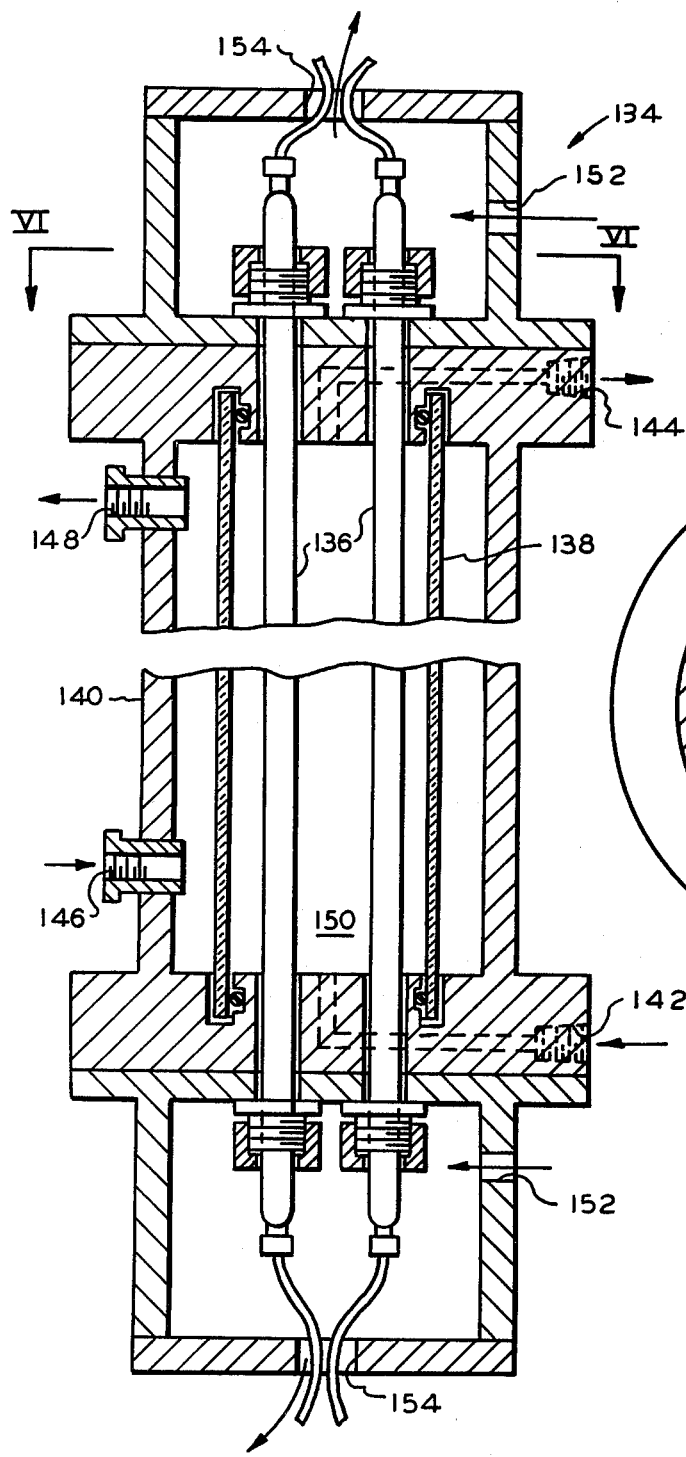
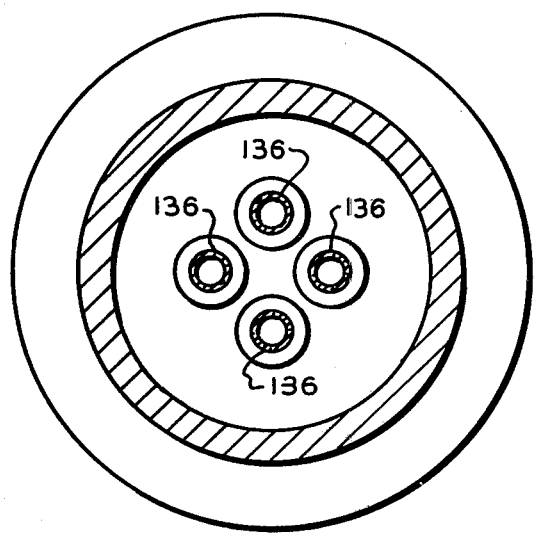
Fig. 6.
Fig. 5

APPARATUS FOR SANITIZING LIQUIDS WITH ULTRA-VIOLET RADIATION AND OZONE

REFERENCE TO PENDING APPLICATION

This application is a continuation of application Ser. No. 879,204, filed Feb. 21, 1978, now abandoned, in the names of Allan J. Coviello for "Apparatus for Sanitizing Liquids".

BACKGROUND OF THE INVENTION

In the treatment of water for drinking purposes or of waste water prior to discharge, it is conventional practice to disinfect the water for elimination of potentially harmful microorganisms. It has long been conventional practice to utilize chlorine in liquid or gaseous form as the biocide to accomplish this task. Recent investigations have pointed out the potential disadvantages of chlorination due to formation of harmful by-products. Interest has increased, therefore, in the use of other biocides such as ultraviolet radiation and ozone.

It is well known that ultraviolet radiation at a wave length of 2537 A is an efficient germicide. This is described by Czulak et al. in U.S. Pat. No. 3,336,099, issued Aug. 15, 1967. It is also known that the output of a lamp designated to produce 2537 A wave length is optimum at a particular operating temperature. Temperatures either warmer or cooler than the optimum will produce lower output of radiation. Further, it is also known that when air is subjected to ultraviolet radiation, at a wave length of 1875 A, that ozone is produced from oxygen contained in the air.

As is disclosed in U.S. Pat. No. 3,336,099, waste water and air can be treated simultaneously by ultraviolet radiation in apparatus having a single lamp, and the treated water can then be contacted in a storage tank by the ozone that is produced to further purify the water. However, the construction and arrangement of the apparatus disclosed in this patent fails to provide the efficiency of ultraviolet radiation to eliminate harmful microorganisms while simultaneously optimizing the ozone production potential from the ultraviolet radiation source. In the disclosure of this patent is is contemplated that the air to be irradiated should be cooled after passing through an air compressor, but when the cooled air is then passed in contact with the lamp it must flow at a sufficiently rapid rate so that if the temperature of the lamp is maintained in a range wherein desired radiation efficiency is achieved, the ozone concentration of the air is relatively low. Thus, high radiation efficiency and optimum ozone concentration cannot be achieved simultaneously.

SUMMARY OF THE INVENTION

The present invention has overcome the inadequacies of the prior art of the type disclosed in U.S. Pat. No. 3,336,099, and provides an improved apparatus for sanitizing liquids which increases the efficiency of ultraviolet radiation to eliminate harmful microorganisms while simultaneously optimizing the ozone concentration potential from the ultraviolet radiation source.

The improved apparatus provides both a means of contacting contaminated water with ultraviolet light to eliminate potentially harmful organisms as well as to provide cooling necessary for efficient operation of the lamp and simultaneous production of ozone for secondary disinfection of the water.

According to the several forms of the invention, a UV lamp is contained within a quartz sleeve which has water to be disinfected contacting its outside. The air space or zone between the quartz sleeve and the UV lamp is provided such that a pump may draw air along the lamp at a desired or optimum rate allowing sufficient contact time for a significant quantity of the oxygen contained in the air to be converted to ozone. The pump then provides the means for contacting the ozone-rich air with the treated water. Also provided is a means for a high voltage of air to be contacted with a portion of the lamp, thereby cooling the lamp and increasing its efficiency over that expected from an uncooled operating lamp.

In certain forms of the present invention, the apparatus includes passageways, providing for separate passage of the cooling air and the air to be irradiated for the production of ozone. In a preferred form, a single inlet for the air is provided and a major portion of this air is diverted for contact at a relatively high velocity with at least one end of the UV lamp, and the remainder of the air is drawn at a lower rate along the length of the lamp for ozone production. In other forms of the invention, separate sources of inlet air are provided and separate passageways extend through the apparatus, one passageway serving to cool only the end portions of the lamp and the other passageway providing for passage of air at a substantially slower rate along the length of the lamp for the production of the ozone; and in another form of the invention a plurality of concentric passageways are provided, the inner one serving as a cooling passage through which air can travel rapidly, and the outer passageway serving to permit the flow of air at a relatively slow rate for the production of ozone.

In still another form of the invention, two-stage air contact is provided wherein the air initially travels rapidly over the one end of the UV lamp because of the small restricted passageway provided, and the second stage is defined by a relatively larger passageway through which the air then flows at a relativley slow rate to provide production of the ozone.

Other objects of this invention will appear in the following description and appended claims, reference being had to the accompanying drawings forming a part of this specification wherein like reference characters designate corresponding parts in the several views.

BRIEF DESCRIPTION OF THE DRAWINGS

FIG. 1 is a vertical section through apparatus embodying one form of the present invention wherein separation of the passage of cooling air and irradiated air is provided;

FIG. 2 is a similar illustration of a second embodiment of the invention wherein separation of cooling air and irradiated air is provided;

FIG. 5 illustrates still another embodiment of the invention similar to that of FIG. 3, but wherein a plurality of ultraviolet lamps are provided;

FIG. 6 is a section taken on the lines 6—6 of FIG. 5; and

DESCRIPTION OF THE PREFERRED EMBODIMENTS

Before explaining the present invention in detail, it is to be understood that the invention is not limited in its application to the details of construction and arrangement of parts illustrated in the accompanying drawings, since the invention is capable of other embodiments and of being practiced or carried out in various ways. Also, it is to be understood that the phraseology or terminology employed herein is for the purpose of description and not of limitation.

Figure 7:
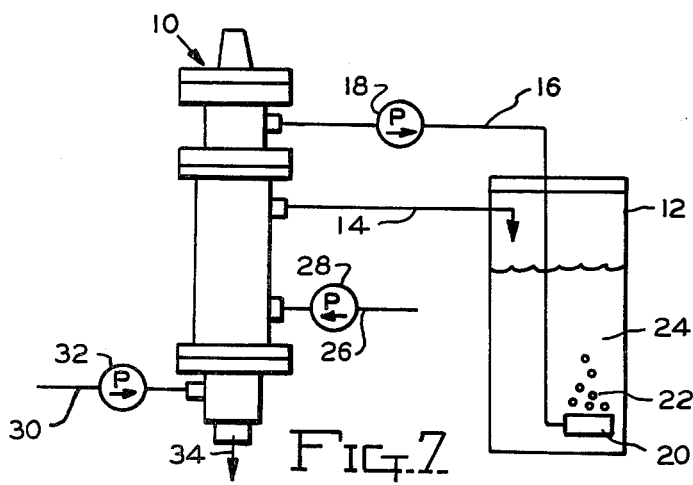
FIG. 7 is a schematic illustration showing the embodiment of FIG. 1 in association with a storage tank for carrying out the treatment of the waste water.

Referring now to the drawings, the invention will be described in greater detail. Attention is directed first to FIG. 7, which shows apparatus 10 that can be any of the embodiments shown in FIGS. 1-5, but in this instance is the embodiment of FIG. 1. Apparatus 10 is illustrated in association with the water storage tank 12 into which the waste water is discharged via the conduit 14 after it has been contacted by ultraviolet light in apparatus 10, and also into which has been discharged the irradiated air containing ozone that has been produced in apparatus 10. The irradiated air and ozone are transferred to the tank 12 via the conduit 16 by means of the air pump 18 at a preselected rate of flow. The irradiated air and ozone are contacted with the water in the tank 12 by means of the air diffuser 20, located adjacent to the bottom of the tank 12. The diffused air 22 passes upward from the air diffuser 20 through the waste water 24 which has been treated previously by exposure to the ultraviolet light. Thus, the ultraviolet light functions to carry out primary disinfection and the ozone in the air functions to carry out secondary disinfection of the waste water.

The waste water is initially delivered to the apparatus 10 via the conduit 26, and any suitable pump means 28 can be used to move the waste water at a desired rate of flow through the apparatus 10 for discharge via the conduit 14 to the tank 12. A single source of air is provided via the conduit 30, and any suitable pump, blower means 32, or the like, can be employed to supply this air. As will be explained subsequently, the cooling air is discharged from the apparatus 10 where indicated by the arrow 34, and a lesser quantity of air which is to be irradiated will pass through the apparatus 10 at the rate permitted by the pump 18 for discharge into the tank 12 as previously described.

Referring now to FIG. 1, details of the apparatus 10, embodying a preferred form of the invention, will now be described. The apparatus 10 includes the conventional elongated ultraviolet lamp 36 and has an electrical receptacle 38 at its upper end. A suitable ultraviolet lamp for this purpose is a standard G-37-T6 ultraviolet lamp.

A bottom end cap assembly 40 encloses the lower end 42 of the ultraviolet lamp 36 and supports the inner duct 44 and the outer duct 46 thereabove. The inner duct is transparent, and is made of a suitable material, such as quartz, which is transparent to the germicidal wave lengths of the ultraviolet light. The outer duct 46 can be made of any suitable material, such as organic plastics or stainless steel, which are not readily succeptable to corrosion caused by the waste water.

Means, including the conduit 30, are provided to pass air through the inner duct 44 so that the air is irradiated and ozone is formed primarily in the zone 48 defined between the ends of the inner duct 44 and the inner diameter of the duct 44. However, a major portion of the air that enters at 30 is used only for cooling ultraviolet lamp 36 and will enter the lower outer sleeve 50 of the bottom cap assembly 40 by way of the inlet port 52 and will then flow around the lower inner sleeve 54 and through the port 56 generally in the direction of the arrow 58 for discharge out of the open lower end of the lower outer sleeve 50, thereby impinging directly upon the lower end of the ultraviolet lamp 36 to cool the same. Lower inner sleeve 54 is connected to the lower outer sleeve 50 at the bottom thereof so that the annular duct formed between these two sleeves is closed at the bottom so that all of the air discharged at 34 must impinge upon ultraviolet lamp 36.

Thus, the major portion of the air that enters via the conduit 30 will discharge at 34 through the lower end of the bottom cap assembly 40 with the minor portion of the air passing upward around the ultraviolet lamp 36 for discharge via the conduit 16. As can be seen in FIG. 1, the air passage available around the lower end 42 of the lamp 36 is relatively small so that the air which discharges at the lower end can flow at a relatively high velocity along the lamp.

The zone 48 which surrounds the middle portion of the lamp 36 has a relatively large inner diameter so that the air which passes through this zone can flow at a relatively slow velocity governed by the rate at which the pump 18 moves the air through this zone. When the irradiated air with ozone leaves the zone 48, it will pass inside the inner upper sleeve 60 to the conduit 16.

As previously indicated, the waste water is introduced into the apparatus 10 via the conduit 26 where it can flow upward through the passageway defined between the duct 44 and the duct 46 for discharge via the conduit 14. When passing upward through the apparatus 10, the waste water will be irradiated by the ultraviolet light from the ultraviolet lamp 36. The top cap assembly 62 can be any conventional construction for holding the ultraviolet lamp 36 and also to provide means for gaining access to the ducts 44 and 46, for cleaning purposes and the like. To provide proper seals at the upper and lower ends of the ducts 44 and 46, conventional O-rings 64 are employed.

In operation of the preferred embodiment shown in FIG. 1, it has been found that very satisfactory results are achieved utilizing cooling air which enters apparatus 10 at approximately 27° C. and which is discharged at the lower end of the bottom cap assembly at a rate of approximately 28 liters per minute while at the same time allowing air to flow through the zone 48 at a rate of from 2.5 liters per minute to 14 liters per minute. Ozone concentrations of from 0.498 to 0.115 milligrams per liter in the air were achieved. Thus, the slowest rate is preferred so that nearly 0.5 milligrams per liter can be obtained. Contacting the lower end of the ultraviolet lamp 36 with cooling air, as specified, resulted in the ultraviolet lamp 36 operating at a relatively high efficiency. This was carried out in conjunction with a lamp of approximately one meter in length. The quartz sleeve or inner duct 44 had an internal diameter of 40 millimeters. Thus, it can be seen that with respect to the relative rate of flow of air discharged at 16 and 34, the rate is very substantially greater at 34 than at 16. Preferably, the rate is at least ten times greater at 34 than at 16 under the described conditions or operation. With respect to the rate of flow of the waste water through the outer duct defined by the sleeve 46, it is known that different organisms require different lethal dosages of ultraviolet radiation, for example, Esherichia coli requires 7040 micro-watt-seconds per cm$^2$, while infectious hepatitis virus require 8000 micro-watt-seconds per cm$^2$. It is therefore desirable that the preferred embodiment whose duct defined by sleeve 46 is of 1.6 liters volume, be operated at less than 62 liters per minute input, and in order to allow an adequate factor of safety, at less than 6.2 liters per minute.

Figure 3:
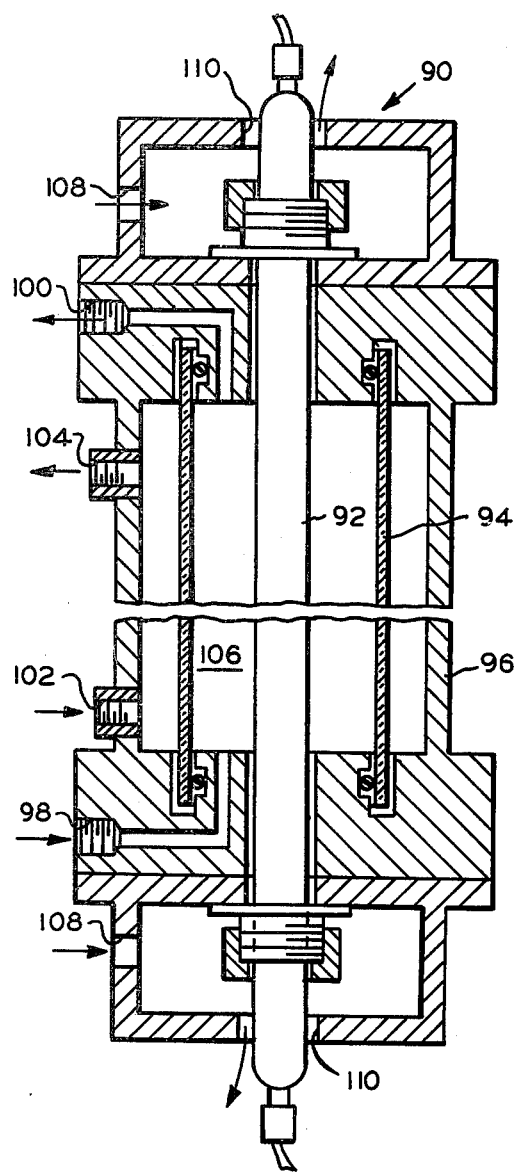
FIG. 3 is a similar illustration of still another embodiment of the invention which also provides separate passageways for flow of cooling air and irradiated air.
Figure 4:
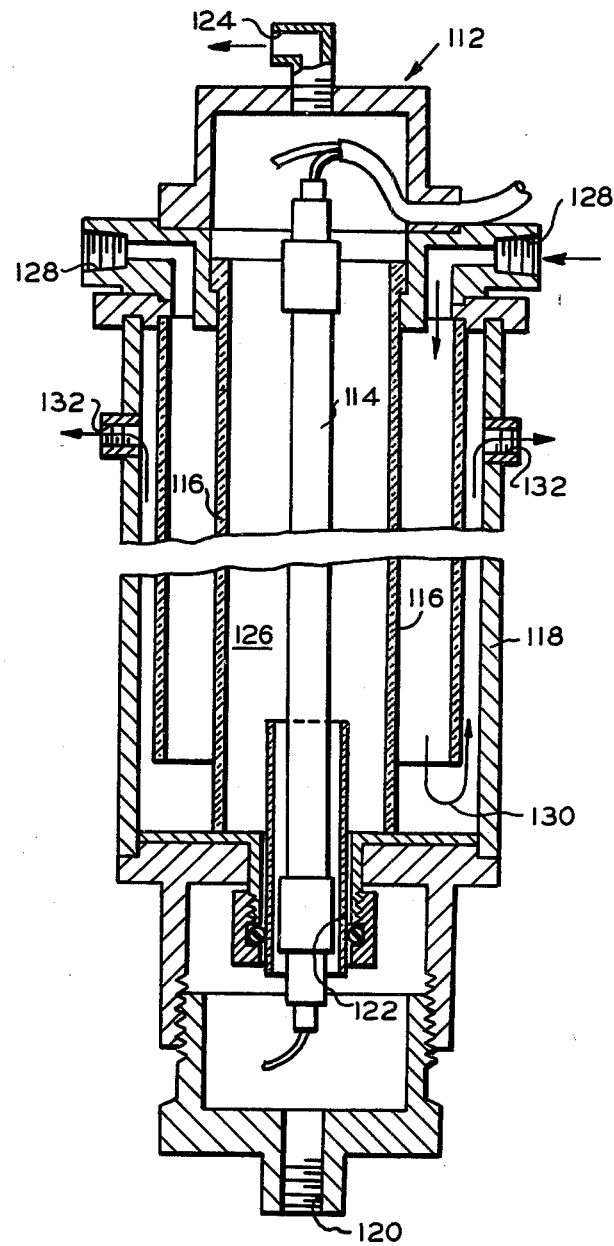
FIG. 4 illustrates still another embodiment of the present invention wherein a single passageway for air is provided, and wherein two stages are provided wherein contact is utilized, one for cooling purposes and the other for irradiation purposes.

Referring next to FIGS. 2, 3 and 4, other embodiments of the invention will be described, with particular reference to the passageways provided for the flow of the waste water and the air. FIG. 2 illustrates an apparatus 66 which includes a conventional ultraviolet lamp 68, an inner duct 70 surrounding the lamp 68 and formed from a material which is transparent to the germicidal wave lengths of the ultraviolet light from the lamp 68. An outer duct 72 surrounds the inner duct 70. This embodiment also includes a cooling duct 74 inside the inner duct 70, also surrounding the ultraviolet lamp 68, and it is formed of quartz or similar material which is transparent to the germicidal wave lengths of the ultraviolet light and to the wave lengths of the ultraviolet light for producing ozone from oxygen contained in air. Means 76 which also may include a pump (not shown), are provided for passing air through the inner duct 70 so that the air is irradiated and ozone is formed from the oxygen therein and is discharged at 78 for passage to the tank 12. Means 80, which may include a pump, (not shown), are provided for passing waste water through the outer duct 72 so that the liquid can be irradiated and then discharged at 82 to the tank 12. In this form of the invention, a zone 84 of relatively large dimension is provided so that the air passing through the inner duct 70 can move at a slow rate to produce a relatively high concentration of ozone.

Means 86, which can also include a pump (not shown), are provided to pass cooling air along the length of the lamp 68 at a relatively fast rate to maintain the lamp 68 at a temperature sufficient to achieve a relatively high radiation output.

In the embodiment illustrated in FIG. 3, apparatus 90 is provided which includes the conventional elongated ultraviolet lamp 92, an inner duct 94 surrounding the lamp 92 and formed from a material which is transparent to the germicidal wave lengths of the ultraviolet light from lamp 92, and an outer duct 96 surrounding the inner duct 94. Means 98, which may include a pump (not shown), are provided for passing air through the inner duct 94 so that the air is irradiated and ozone is formed. The irradiated air containing ozone is then discharged at 100 to the tank 12. Means 102, which may include a pump (not shown), are provided to pass waste water through the outer duct 96 so that the liquid is irradiated and can be discharged at 104 to the tank 12. In this form of the invention the inner duct 94 includes a zone 106 wherein the air will flow at a pedetermined relatively slow rate so that when irradiated, it will produce a relatively high concentration of ozone. Also, this embodiment of the invention includes means 108 at the upper and lower ends of apparatus 90 to pass cooling air along portions of the length of the lamp 92 at a relatively high rate to maintain the lamp 92 at a temperature sufficient to achieve relatively high radiation output. This air can then be discharged at 110. The means to pass cooling air may include suitable pump means (not shown).

In the embodiment of the invention illustrated in FIG. 4, apparatus 112 includes a conventional elongated ultraviolet lamp 114, an inner duct 116 surrounding the lamp 114 and formed from a material which is transparent to the germicidal wave lengths of the ultraviolet light from lamp 114, and an outer duct 118 surrounding the inner duct 116. Means 120, which may include a pump (not shown), are provided to pass air through the inner sleeve 122, which may be made of a suitable material, such as quartz, and then through the inner duct 116 for discharge at 124 to the tank 12. This air will be irradiated when passing through the enlarged zone 126 and ozone will be formed. Means 128, which may include a pump (not shown), are provided to pass liquid through the outer duct 118 in the path indicated by arrows 130 and discharge at 132 to the tank 12. During passage, this water will be irradiated from the ultraviolet light emitted by lamp 114. Also in this embodiment, the zone 126 is substantially larger in diameter or effective cross section than the passage provided between the sleeve 122 and the lamp 114 so that the air entering at 120 will in a first state of operation flow rapidly in contact with at least a portion of a lamp 114 after which it will flow at a relatively slow rate through the zone 126. Passage through the first stage will effect cooling of the lamp 114 and passage through the second stage will effect optimum production of ozone.

In the embodiment of the invention in FIG. 5, apparatus 134 is provided which includes a plurality of conventional elongated ultraviolet lamps 136, an inner duct 138 surrounding the lamps 136 and formed from a material which is transparent to the germicidal wave lengths of the ultraviolet light from lamps 136, and an outer duct 140 surrounding the inner duct 138. Means 142, which may include a pump (not shown), are provided for passing air through the inner duct 138 so that the air is irradiated and ozone is formed. The irradiated air containing ozone is then discharged at 144 to the tank 12. Means 146, which may include a pump (not shown), are provided to pass waste water through the outer duct 140 so that the liquid is irradiated and can be discharged at 148 to the tank 12. In this form of the invention the inner duct 138 includes a zone 150 wherein the air wll flow at a predetermined relatively slow rate so that when irradiated, it will produce a relatively high concentration of ozone. Also, this embodiment of the invention includes means 152 at the upper and lower ends of the apparatus 134 to pass cooling air along portions of the length of the lamps 136 at a relatively high rate to maintain the lamps 136 at a temperature sufficient to achieve relatively high radiation output. This air can then be discharged at 154. The means to pass cooling air may include suitable pump means (not shown).

This form of the invention has the advantage that a large zone 150 can be utilized to provide a relatively high concentration of ozone and the lamps are also in close proximity to the waste water flowing in outer duct 140 which serves a two-fold purpose of using the germicidal wave lengths of the lamps 136 to the maximum potential and also of using cooling effect on the lamps that can be derived from the flow of the waste water in a heat-exchange relationship.

From the foregoing description it will be evident that in all of the embodiments described, air is introduced into the apparatus 10, 66, 90, 112 and 134 to produce optimum cooling of the ultraviolet lamps therein by movement of the air at a relatively high velocity along at least a portion of the length of the lamp, and air is also moved at a relatively slow rate through a zone exposed to the ultraviolet light so that optimum production of ozone is realized. Simultaneously, the waste water is treated with the ultraviolet light, and the rate of flow of the waste water is set so that optimum germicidal treatment occurs.

It is claimed:

1. Apparatus for sanitizing liquids comprising an elongated ultraviolet lamp, an inner duct surrounding the lamp and formed from a material which is transparent to the germicidal wavelengths of the ultraviolet light, an outer duct surrounding said inner duct, means to pass air through said inner duct so that said air is irradiated and ozone is formed, means to pass a liquid through said outer duct so that said liquid is irradiated, a tank, and means to pass the irradiated liquid and the irradiated air into said tank, the improvement comprising said inner duct including a zone wherein said air will flow at a predetermined relatively slow rate so that the air that is irradiated will produce a relatively high concentration of ozone, and air means to pass cooling air along at least a portion of the length of the lamp at a relatively high velocity to maintain the lamp at a temperature sufficient to achieve a relatively high radiation output.

2. Apparatus that is defined in claim 1, wherein said improvement includes two-stage air contact of said lamp to provide irradiation of the air and cooling of the lamp, said inner duct including a relatively large diameter sleeve that defines said zone and through which the air moves slowly to increase ozone concentration in one of the stages, and said means to pass cooling air includes at least one relatively smaller diameter sleeve through which the air must flow at a higher velocity to promote cooling in the other of the stages.

3. Apparatus that is defined in claim 1, wherein said improvement includes separate passage of the irradiated air and the cooling air, said inner duct surrounding the midportion of said lamp inward from the ends of the lamp and providing passage for the irradiated air only along said midportion at a relatively slow rate, and said means to pass cooling air enclosing at least one of the ends of said lamp and providing for passage of the cooling air at a relatively high velocity.

4. Apparatus that is defined in claim 1, wherein said improvement includes separate passage of the irradiated air and the cooling air, said means to pass cooling air including a cooling duct inside said inner duct and which surrounds said lamp and is formed of a material which is transparent to the germicidal wave-lengths of the ultraviolet light and to the wave-lengths of the ultraviolet light for producing ozone from oxygen contained in air, said cooling air passing through said cooling duct at a relatively high velocity and said irradiated air passing through said inner duct at a relatively slow rate.

5. Apparatus that is defined in claim 1, wherein said improvement includes means providing a common inlet port for the air and separate passage of the irradiated air and the cooling air to separate outlet ports, and said means to pass cooling air includes a baffle for directing a portion of the incoming air through said inner duct at a relativley slow rate and for directing the remainder of the incoming air as a coolant over one end of the lamp at a relatively higher velocity.

6. Apparatus that is defined in claim 1, wherein said means to pass air includes a bottom cap assembly above which are supported said inner and outer ducts and which has a lower outer sleeve into which the lower end of said lamp extends, said lower outer sleeve having an inlet port in the side thereof for receiving air and being open at the bottom for discharge of cooling air, and a lower inner sleeve surrounding the lower end of said lamp and extending upward toward said inner duct, said lower inner sleeve being spaced from said lower outer sleeve and connected at the bottom thereto to provide an annular duct for air to pass upward from said inlet port, said lower inner sleeve also having a port through which air can pass from said annular duct into contact with said lamp and then to be discharged through the bottom open end of said lower outer sleeve so that a major portion of the air entering said lower outer sleeve can be removed rapidly through the bottom open end for cooling the lower end of said lamp and the remainder can pass relatively slowly upward through said inner duct to be irradiated.

7. Apparatus that is defined in claim 1, wherein said improvement includes an air pump in said air means to pass the irradiated air into said tank, said air pump being operable to control the rate that the air flows through said zone.

8. Apparatus that is defined in claim 1, wherein said improvement includes a plurality of ultraviolet lamps that are surrounded by said inner duct, said lamps being arranged in parallel relationship to the longitudinal axis of said inner duct and positioned radially outwardly of the axis to locations adjacent to the inner duct.

9. Apparatus for sanitizing liquids comprising an elongated ultraviolet lamp, an inner duct surrounding the lamp and formed from a material which is transparent to the germicidal wave lengths of the ultraviolet light, an outer duct surrounding said inner duct, means to pass air through an axially extending zone of said inner duct at a predetermined relatively slow rate sufficient so that said air is irradiated and ozone is formed at a relatively high concentration, means to pass cooling air along at least a portion of the length of the lamp at a relatively high velocity sufficient to cool the lamp to a temperature near that which will enable maximum radiation output of the lamp to be achieved, and means to pass a liquid through said outer duct so that said liquid is irradiated.

10. Apparatus that is defined in claim 9, wherein said means that passes air through said zone moves the air at a rate of 1/10 or less than that which said means to pass cooling air moves the cooling air.

11. Apparatus for irradiating air for use in sanitizing liquids comprising an elongated ultraviolet lamp, a duct surrounding the lamp, means to pass air through an axially extending zone of said duct at a predetermined relatively slow rate sufficient so that said air is irradiated and ozone is formed at a relatively high concentration, and means to pass cooling air along at least a portion of the length of the lamp at a relatively high velocity sufficient to cool the lamp to a temperature near that which will enable maximum radiation output of the lamp to be achieved.

12. Apparatus for sanitizing liquids comprising an elongated ultraviolet lamp, a duct surrounding the lamp, means to pass air through said duct so that said air is irradiated and ozone is formed, a tank for storage of liquid, and means to pass the irradiated air into said tank, the improvement comprising said duct including a zone wherein said air will flow at a predetermined relatively slow rate so that the air that is irradiated will produce a relatively high concentration of ozone, and air means to pass cooling air along at least a portion of the length of the lamp at a relatively high velocity to maintain the lamp at a temperature sufficient to achieve a relatively high radiation output.

13. Apparatus that is defined in claim 12, wherein said improvement includes two-stage air contact of said lamp to provide irradiation of the air and cooling of the lamp, said duct including a relatively large diameter sleeve that defines said zone and through which the air moves slowly to increase ozone concentration in one of the stages, and said means to pass cooling air includes at least one relatively smaller diameter sleeve through which the air must flow at a higher velocity to promote cooling in the other of the stages.

14. Apparatus that is defined in claim 12, wherein said improvement includes separate passage of the irradiated air and the cooling air, said duct surrounding the midportion of said lamp inward from the ends of the lamp and providing passage for the irradiated air only along said midportion at a relatively slow rate, and said means to pass cooling air enclosing at least one of the ends of said lamp and providing for passage of the cooling air at a relatively high velocity.

15. Apparatus that is defined in claim 12, wherein said improvement includes separate passage of the irradiated air and the cooling air, said means to pass cooling air including a cooling duct inside the first-named duct and which surrounds said lamp and is formed of a material which is transparent to the wave-lengths of the ultraviolet light for producing ozone from oxygen contained in air, said cooling air passing through said cooling duct at a relative high velocity and said irradiated air passing through said first-named duct at a relatively slow rate.

16. Apparatus that is defined in claim 12, wherein said improvement includes means providing a common inlet port for the air and separate passage of the irradiated air and the cooling air to separate outlet ports, and said means to pass cooling air includes a baffle for directing a portion of the incoming air through said duct at a relatively slow rate and for directing the remainder of the incoming air as a coolant over one end of the lamp at a relatively higher velocity.

* * * * *